Figure 1:
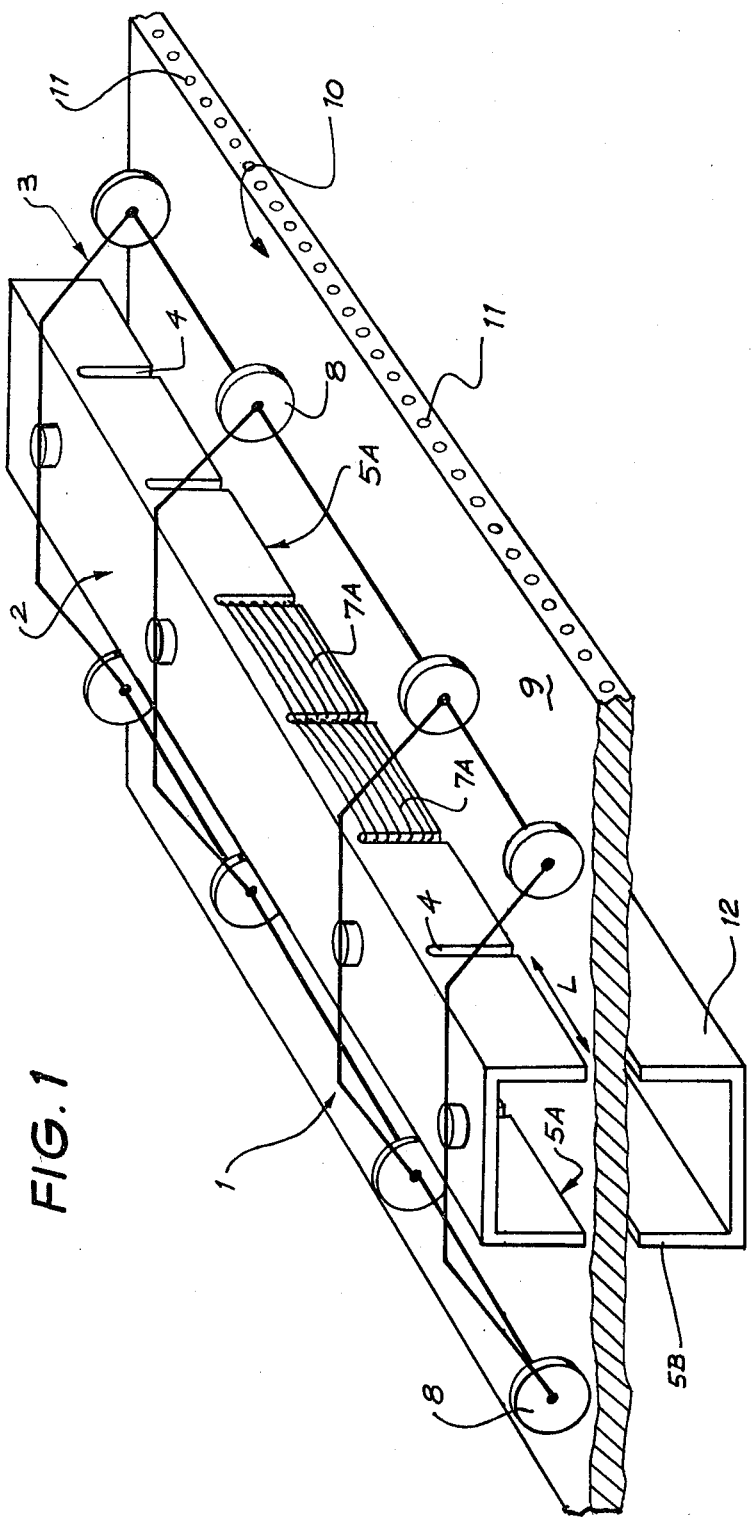

United States Patent [19]

Harrison

[11] 4,439,731
[45] Mar. 27, 1984

[54] MONITORING OF ELONGATE MAGNETICALLY PERMEABLE MEMBERS

[75] Inventor: Alexander Harrison, Beecroft, Australia

[73] Assignee: Commonwealth Scientific and Industrial Research Organization, Australia

[21] Appl. No.: 195,311

[22] Filed: Oct. 8, 1980

[51] Int. Cl.$^3$ .................. G01N 27/82; G01R 33/12
[52] U.S. Cl. .................................. 324/239; 324/243
[58] Field of Search ........ 324/222, 228, 234, 236–243, 324/225; 340/673–677; 198/856

[56] References Cited

U.S. PATENT DOCUMENTS

| | | | |
|---|---|---|---|
| 2,467,306 | 4/1949 | Habig | 324/242 |
| 2,582,437 | 1/1952 | Jezewski et al. | 324/241 |
| 3,444,458 | 5/1969 | Scott | 324/243 |
| 3,792,459 | 2/1974 | Snyder | 340/676 |
| 4,258,319 | 3/1981 | Shimada et al. | 324/242 |

FOREIGN PATENT DOCUMENTS 1270821  4/1972  United Kingdom ................ 324/243

Primary Examiner—Gerard R. Strecker
Assistant Examiner—Walter E. Snow
Attorney, Agent, or Firm—Lyon & Lyon

[57] ABSTRACT

The present invention discloses both a method and apparatus whereby the integrity of elongate magnetically permeable member(s) can be determined even if coated with a non-magnetic substance or embedded in a non-magnetic body. A magnetic yoke having field winding(s) and sensing winding(s) is used to induce a time varying magnetic field in the magnetically permeable member(s). Changes in the reluctance experienced by this magnetic field alter the output of the sensing winding(s). The invention finds particular application to testing conveyor belts, but is also applicable to steel cables, and both rubber and concrete bodies, including steel reinforcing.

25 Claims, 20 Drawing Figures

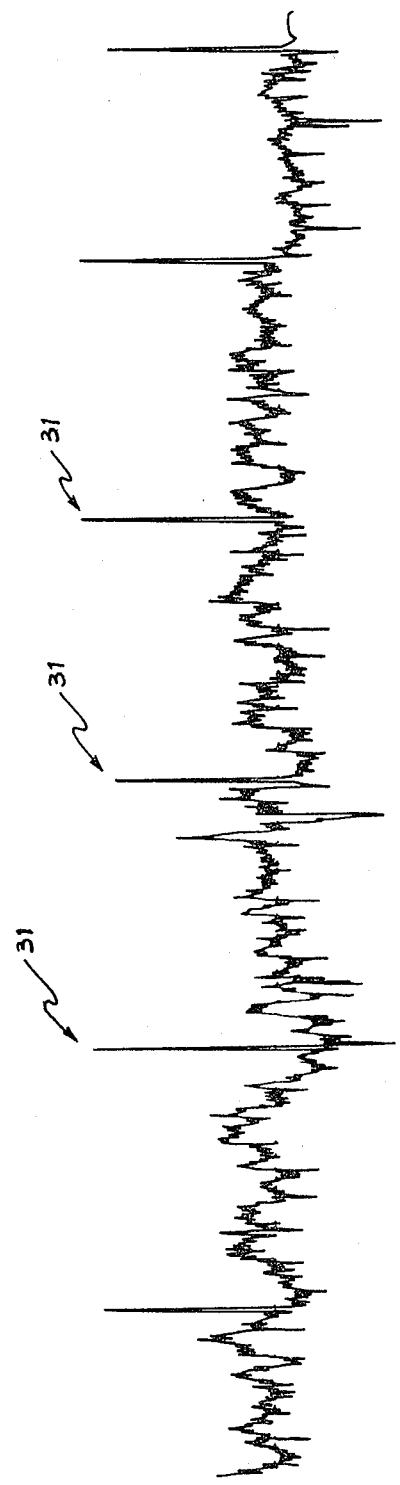

MONITORING OF ELONGATE MAGNETICALLY PERMEABLE MEMBERS

This invention seeks to provide an improved technique and instrument for monitoring gradual metal loss in cables, reinforced belts, rods and rails while they are in service, the metal loss being due to wear, corrosion, breakage or stretch—any reduction in metal section being taken as effective metal loss.

While the technique is an electromagnetic one and the invention will be described in relation to steel cables and rails, it is not confined thereto as it is applicable to monitoring loss of metals normally considered to be non-magnetic, such as brass, but which become magnetically permeable under high-frequency electromagnetic fields. Also, while particular reference will be made to the detection of metal loss in conveyor belts, it will be clear that the invention is not limited thereto.

Conveyor belts commonly employed in the mining industry are formed from long strips of rubber or other elastomeric material within which longitudinal steel cables or cords are embedded. As the rubber surface wears or is damaged, the steel reinforcing is exposed to corrosion which is often difficult to detect by an examination of the surface of the belt, particularly while it is in use. To stop long conveyor belts for regular visual inspection, or to allow the belts to run until they break, is of course costly and it is common practice to discard belts after a given period of use, but much servicable belt is discarded in this way. Similar dilemmas exist in regard to the inspection of steel haulage cables.

It is known that the breakage of steel strands or wires in haulage cables can be monitored electromagnetically while the cable is in use by magnetising it at one point and encircling it with a search coil at another point immediately "downstream" from the first to detect magnetic anomalies formed at strand breaks as they move through the detecting coil. Such anomalies have also been detected by propagating elastic waves along wire rope by the use of magnetostrictive transducers; see for example U.S. Pat. No. 2,656,714. However, neither of these techniques are effective in monitoring the total mass of metal present or the gradual loss of metal through corrosion or wear.

Known alternating current techniques are, in general, based upon the generation of eddy currents in the cable by electromagnetic induction and the detection of these eddy currents through use of a search coil downstream of the electromagnet. Again, this technique is not sensitive to gradual metal loss and, moreover, is dependent upon the speed at which the test piece passes through the transducers relative to the rate at which the eddy currents decay. A technique of this type is described in Australian Patent No. 216676.

Not only do the above techniques have serious disadvantages when applied to individual wire ropes or rods, but they are quite inappropriate for application to conveyor belts of up to a meter or more in width and containing as many as 50 embedded reinforcing cords. It has been proposed (see U.S. Pat. Nos. 4,020,945 and 3,899,071) to detect stretch and tears or other physical damage in such belts by incorporating magnets or conductive loops in the belt material during manufacture so that a transducer can be magnetically or inductively coupled thereto and, when the belt is torn and the magnet or loop broken, an alarm can be sounded. Not only are such belts expensive to manufacture, but the technique does not allow monitoring of gradual metal loss, stretching of splices or the monitoring of conventional belts.

Accordingly, the present invention seeks to provide an instrument and technique for monitoring the effective loss of metal from bodies such as steel cables and steel-cord reinforced conveyor belts in a non-destructive fashion while the cables, belts or the like are in normal use.

The present invention is based upon the realisation that a transformer-effect provides a sound basis for monitoring overall metal loss, especially with suitable design of the transducer, giving compensation for, or minimisation of, relative movement of the test piece and transducer, and/or by comparing the "signature" of a new belt when it is first installed with signatures obtained in the same belt after some period of use.

According to one aspect of the present invention, the instrument includes a transducer comprising: a magnetically permeable U-shape body formed so as to define a pair of spaced poles having substantially co-planar faces, one pole being divided into sections by deep slots formed in its face, exciting coils wound around said sections and interconnected so as to create a substantially uniform magnetic field between and along the pole faces when said coils are energized with alternating electric current, at least one sensor coil wound about the other pole (or portion thereof) so that, in use, an alternating electric potential will be induced in the sensor coil when a metallic body being monitored is located in proximity to and across the pole faces, the magnitude of said signal being related to the amount of magnetically permeable metal in the portion of the body between the pole faces.

Preferably, the transducers are arranged to substantially encircle or encompass the periphery of the body which is to be tested so that the effect of movement of the body away from one portion of the pole faces will be compensated by the movement of the body toward another. It is also preferable to employ mechanical guide means such as rollers or the like, fixed with respect to the transducer, so as to guide the test body therethrough.

From another aspect the invention also includes a technique for monitoring metal loss from steel-reinforced conveyor belts or steel cables and the like wherein the belt or cable is passed through the above described transducer, a signal is derived from the sensing coil (using appropriate filtering, clipping or processing methods) and electronically recorded to provide a first signature, a second signature is derived and recorded in the same way some time later, and wherein the first and second signatures are electronically compared and a signal is derived from the difference between them to indicate the degree and location of metal loss (or other faults) along the cords or strands and/or to activate an alarm upon the defects reaching a predetermined magnitude.

According to a further aspect of the invention there is disclosed a method of monitoring the integrity of an elongate magnetically permeable member, said method comprising the steps of aligning said member between two spaced apart megnetically permeable pole faces separated by a magnetically permeable yoke carrying a field winding and a sensing winding; inducing a time varying magnetic field in said yoke which passes through said elongate member between said pole faces; causing relative movement between said elongate member and said pole faces; and sensing changes in the magnitude of the voltage induced in said sensing winding caused by changes in the reluctance path containing said yoke and said elongate member.

According to a still further aspect of the invention there is disclosed apparatus for monitoring the integrity of an elongate magnetically permeable member, said apparatus comprising a magnetically permeable yoke having two pole faces and being adapted for movement relative to said member; a field winding and a sensing winding carried by said yoke; spacing means to maintain said pole faces spaced a predetermined distance from said elongate member; current generating means connected to said field winding to induce a time varying magnetic field passing through said elongate member between said pole faces; and sensing means connected to said sensing winding to sense the voltage induced therein by said magnetic field.

Figure 2:
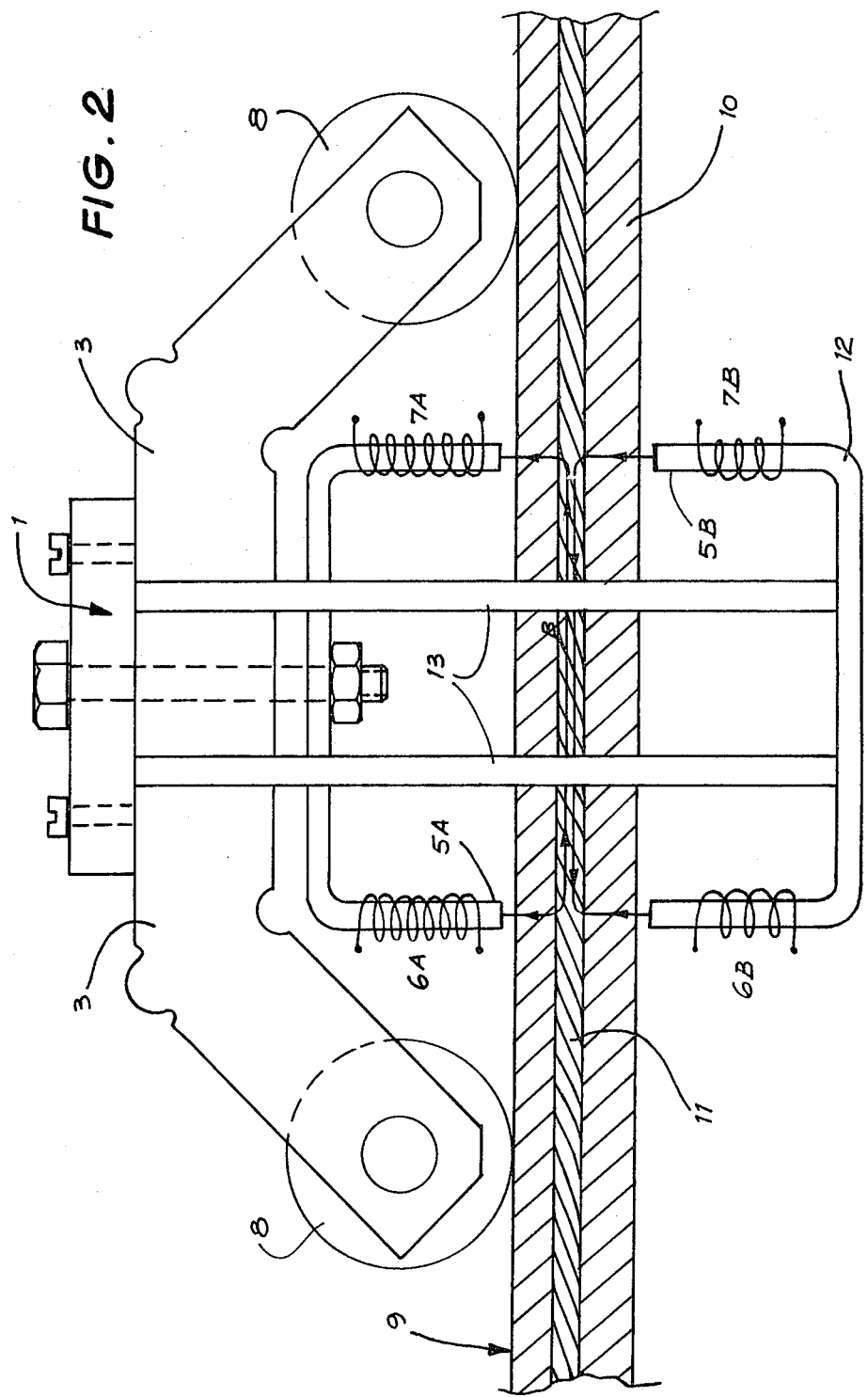
Figure 3:
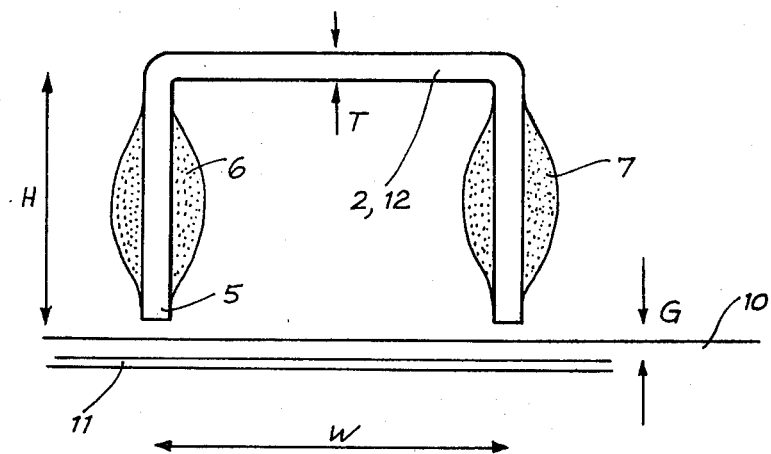
Figure 4:
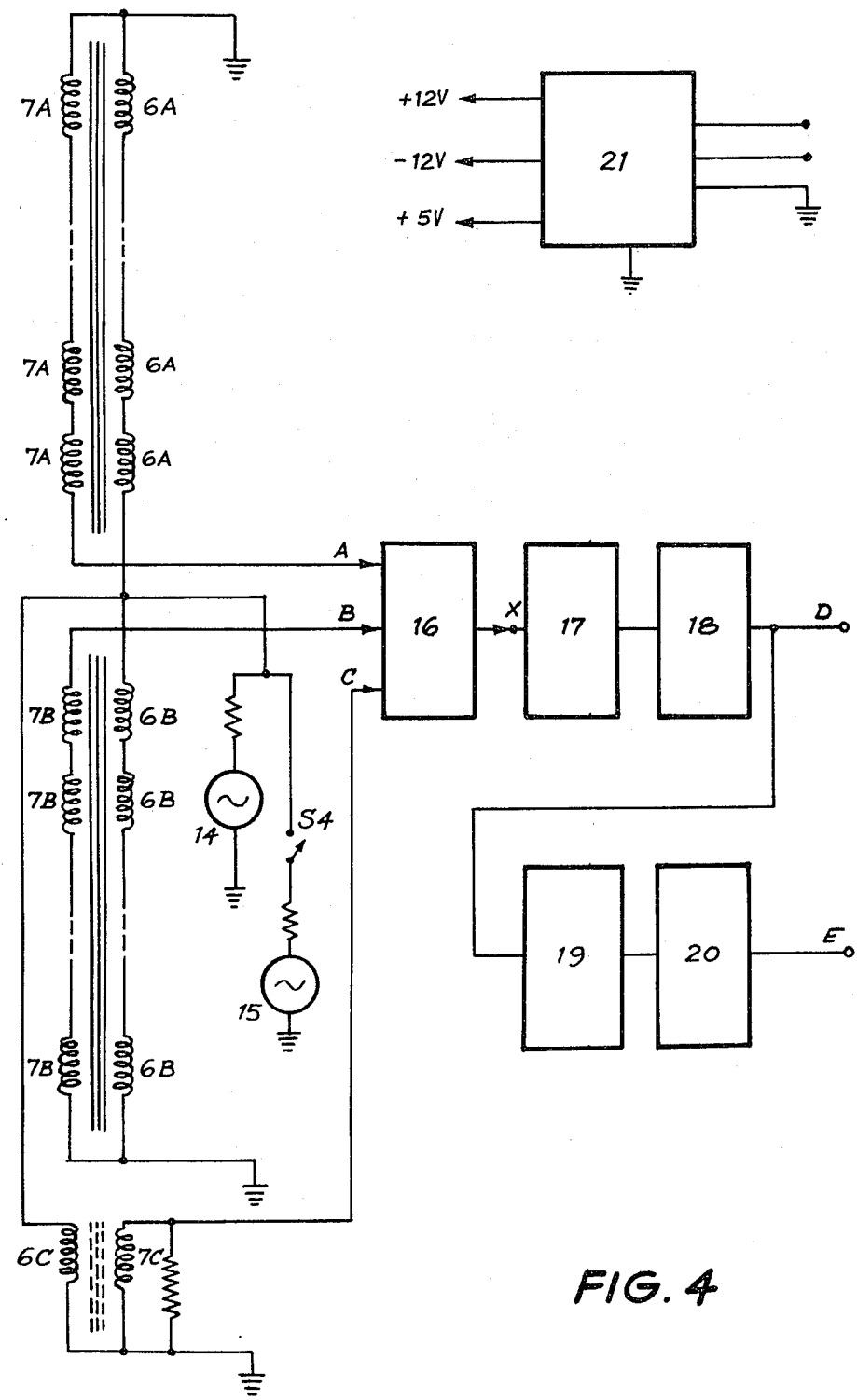
Figure 5:
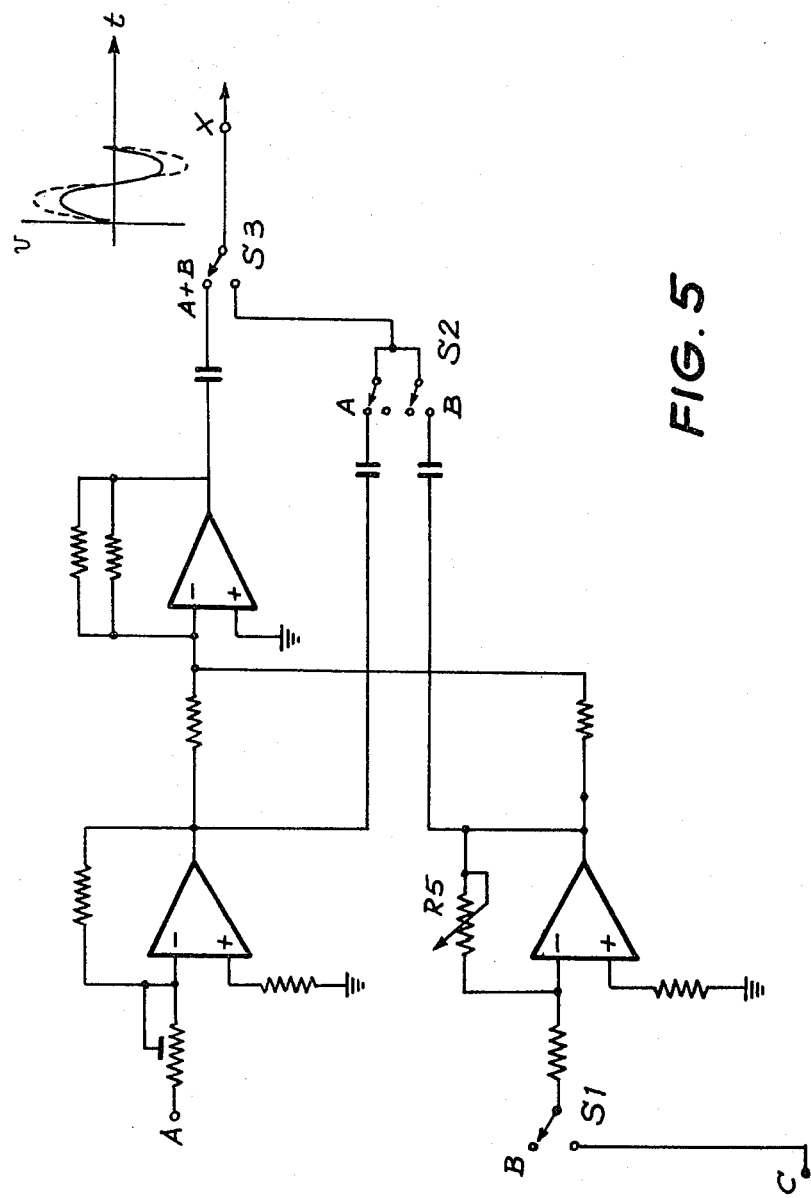
Figure 6:
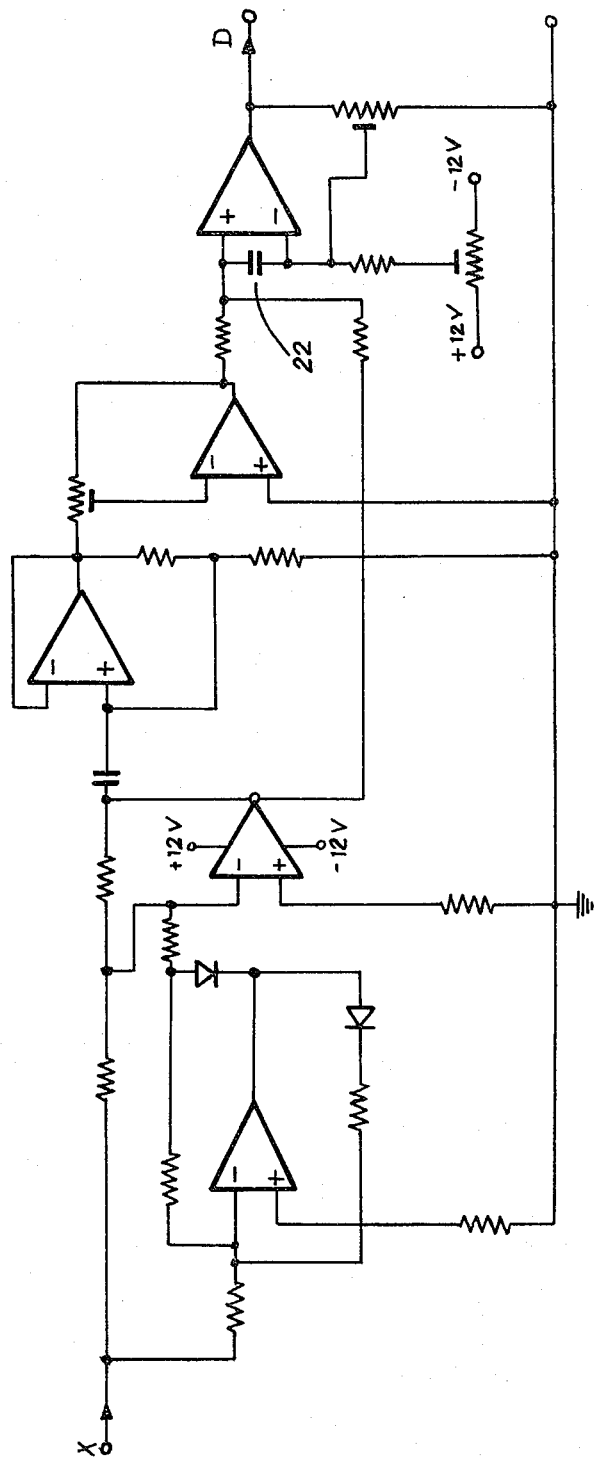

In order to further portray the nature of the present invention, a few particular examples will be described by way of illustration only. In the following description reference will be made to the accompanying drawings in which:

FIG. 1 is a schematic perspective and partly cross-sectional view of the apparatus of the preferred embodiment, FIG. 2 is a side elevation of the apparatus of FIG. 1, FIG. 3 is a schematic cross-sectional view of the upper magnetic yoke of FIGS. 1 and 2, FIG. 4 is a block diagram of the electric sensing circuit used in conjunction with the apparatus of FIGS. 1 to 3, FIG. 5 is a circuit diagram of the input interface block 16 of FIG. 4, FIG. 6 is a circuit diagram of blocks 17 and 18 of FIG. 4.

Figure 8:
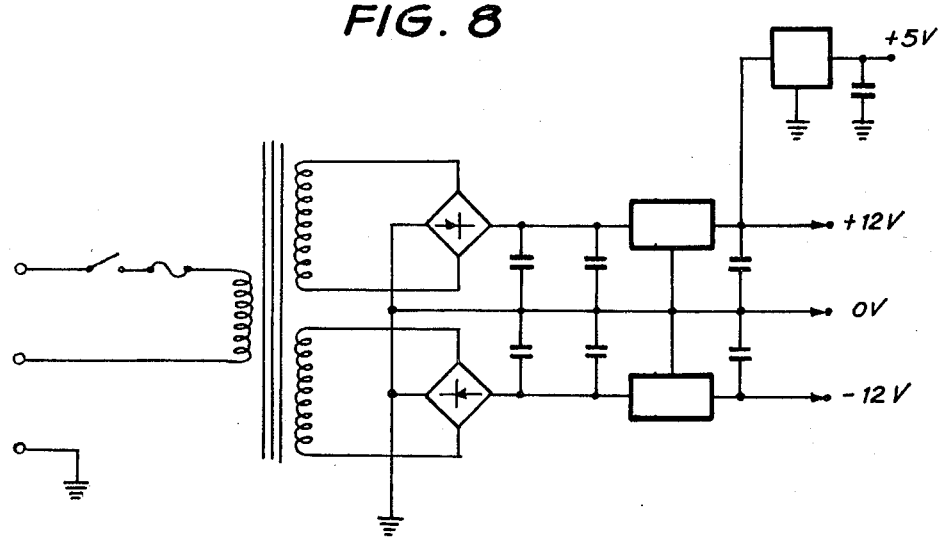
Figure 7:
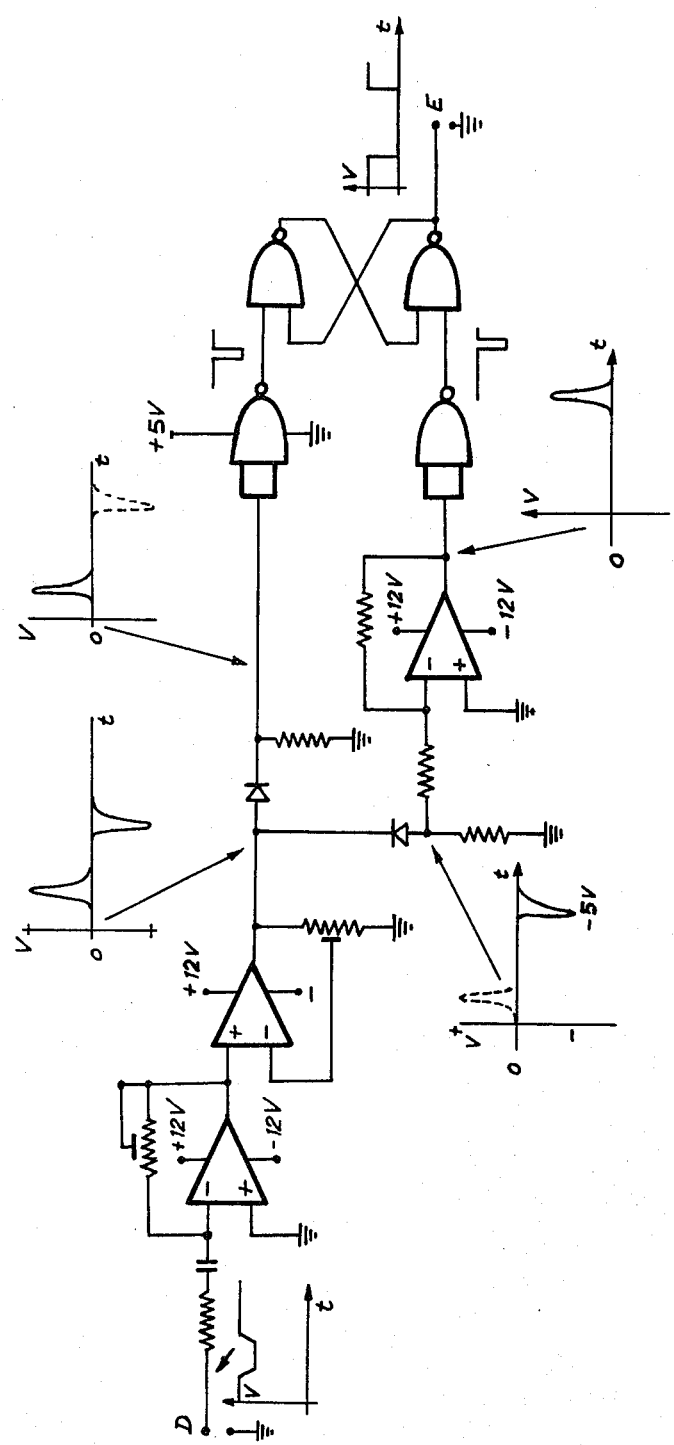
Figure 10:
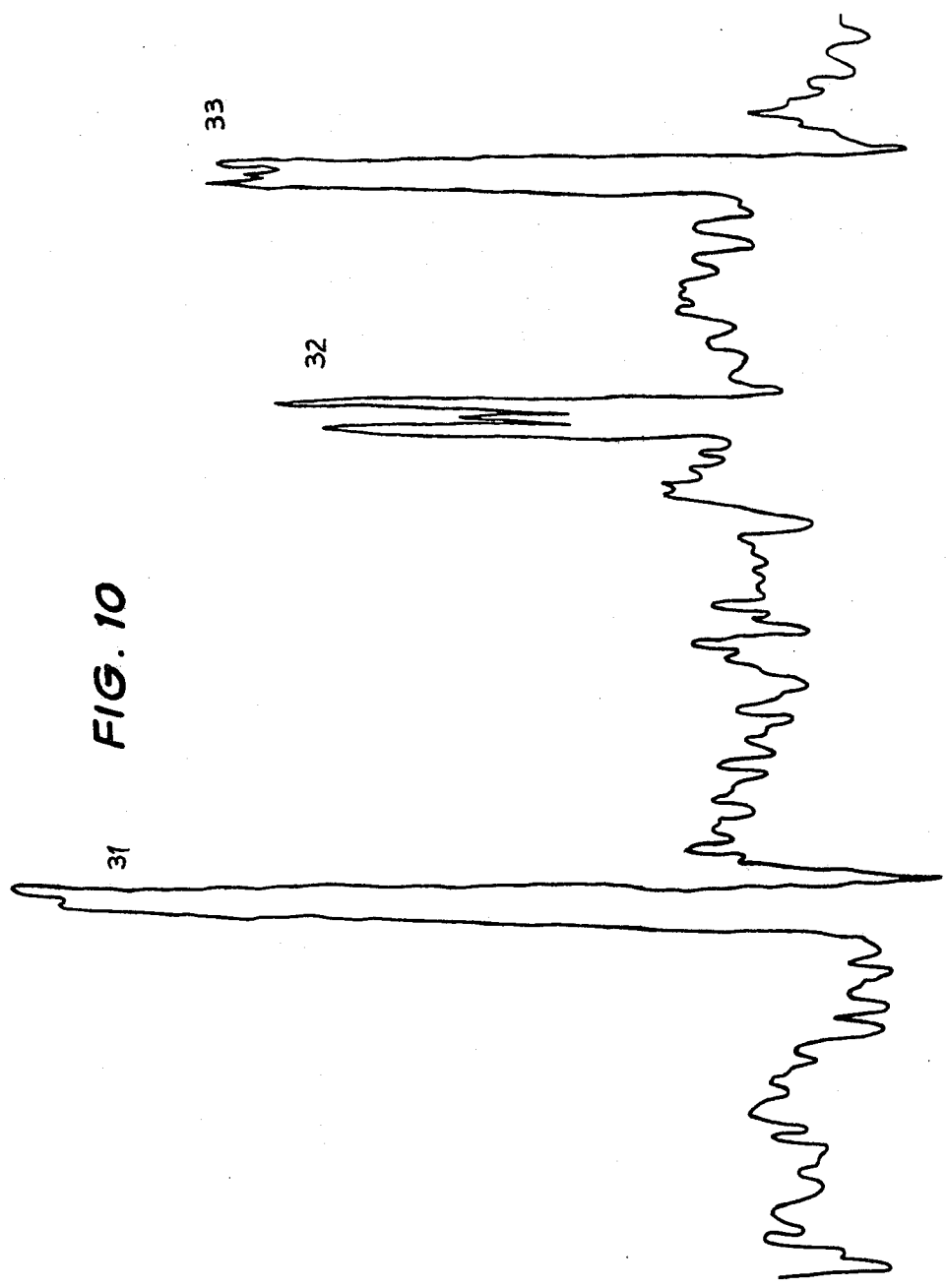
Figure 11:
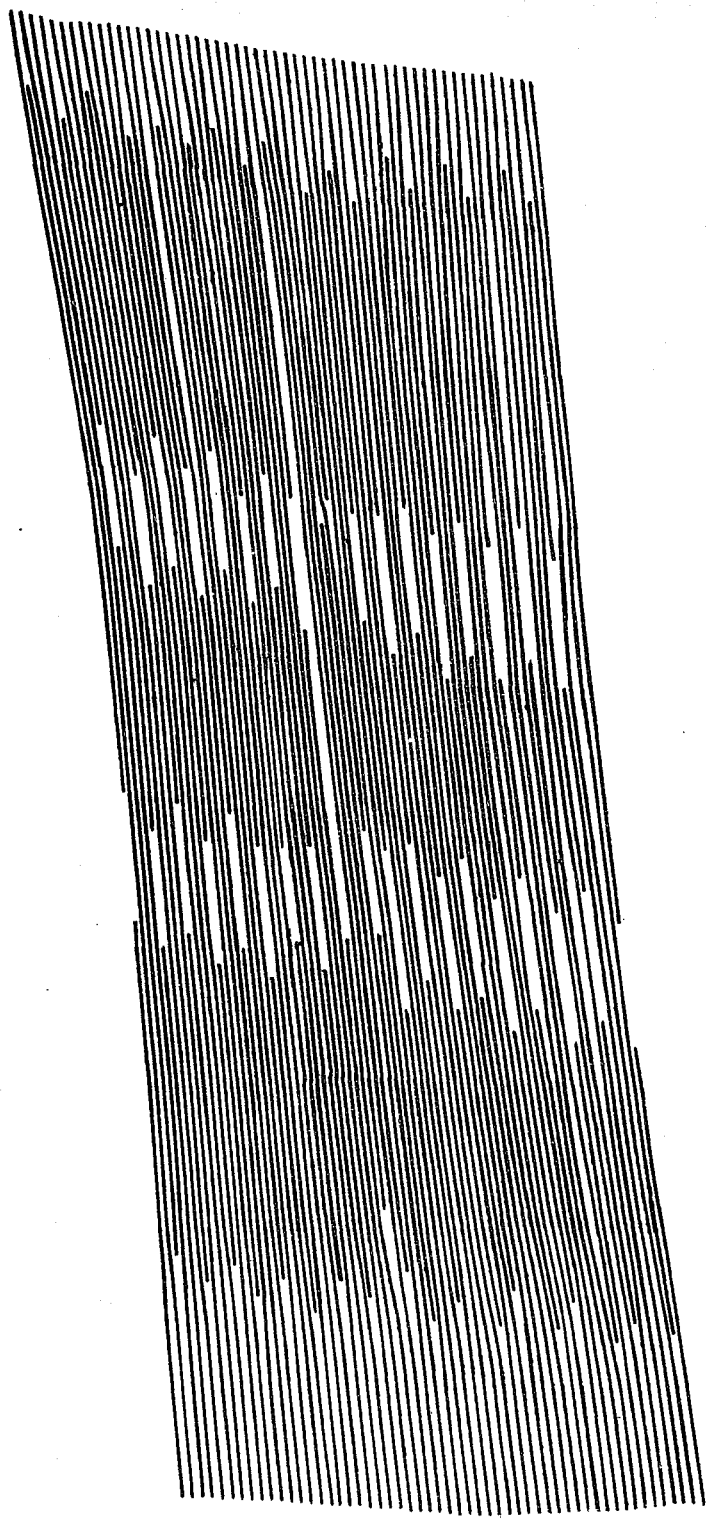
Figure 12:
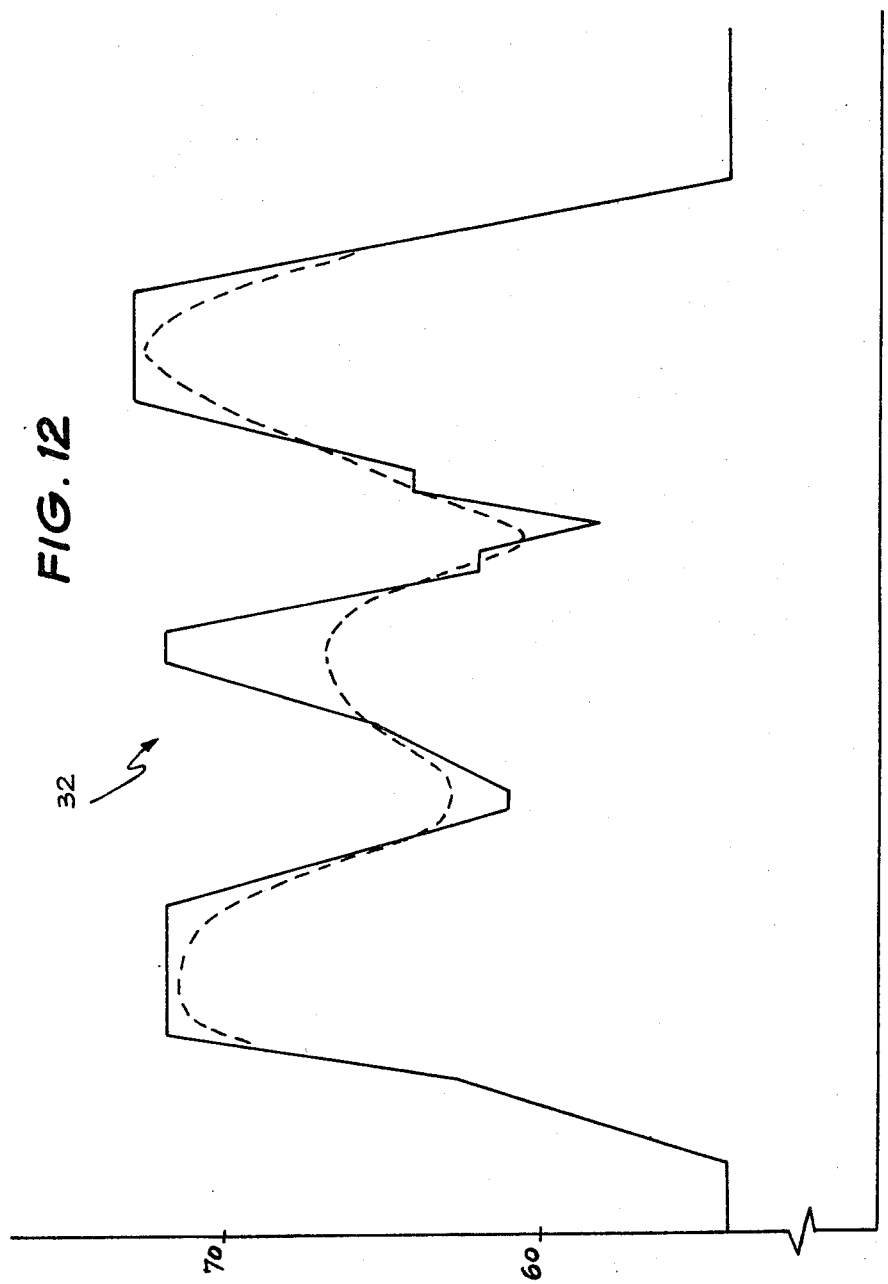
Figure 13:
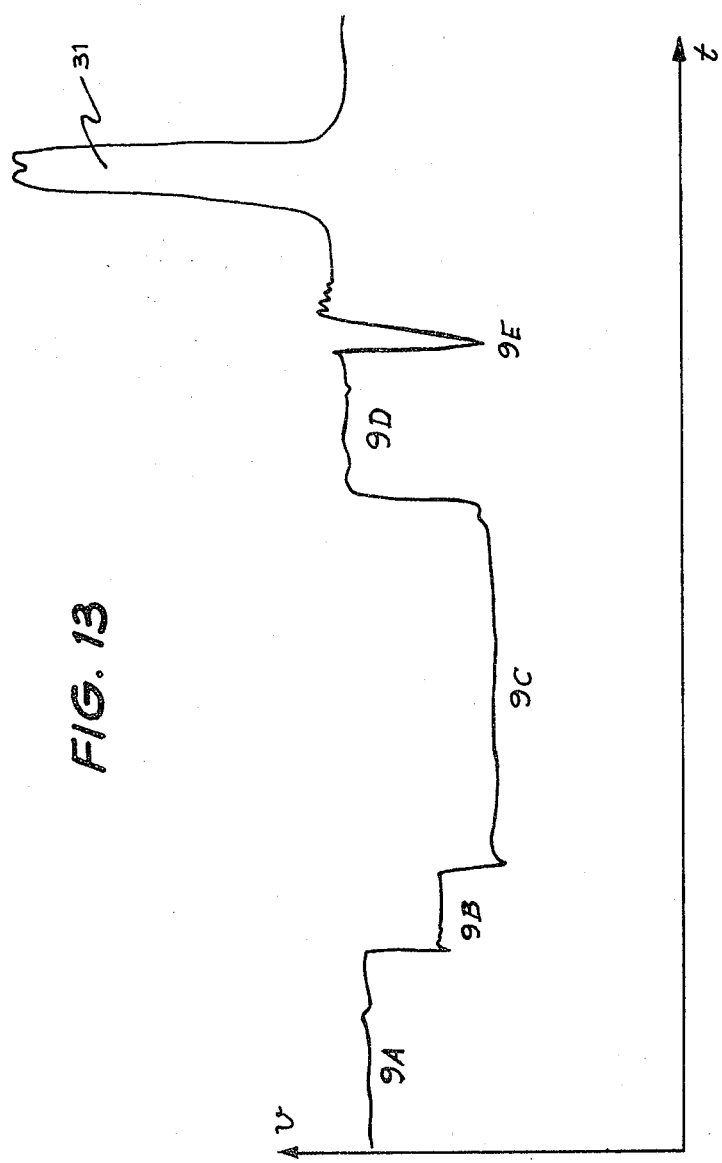
Figure 14:
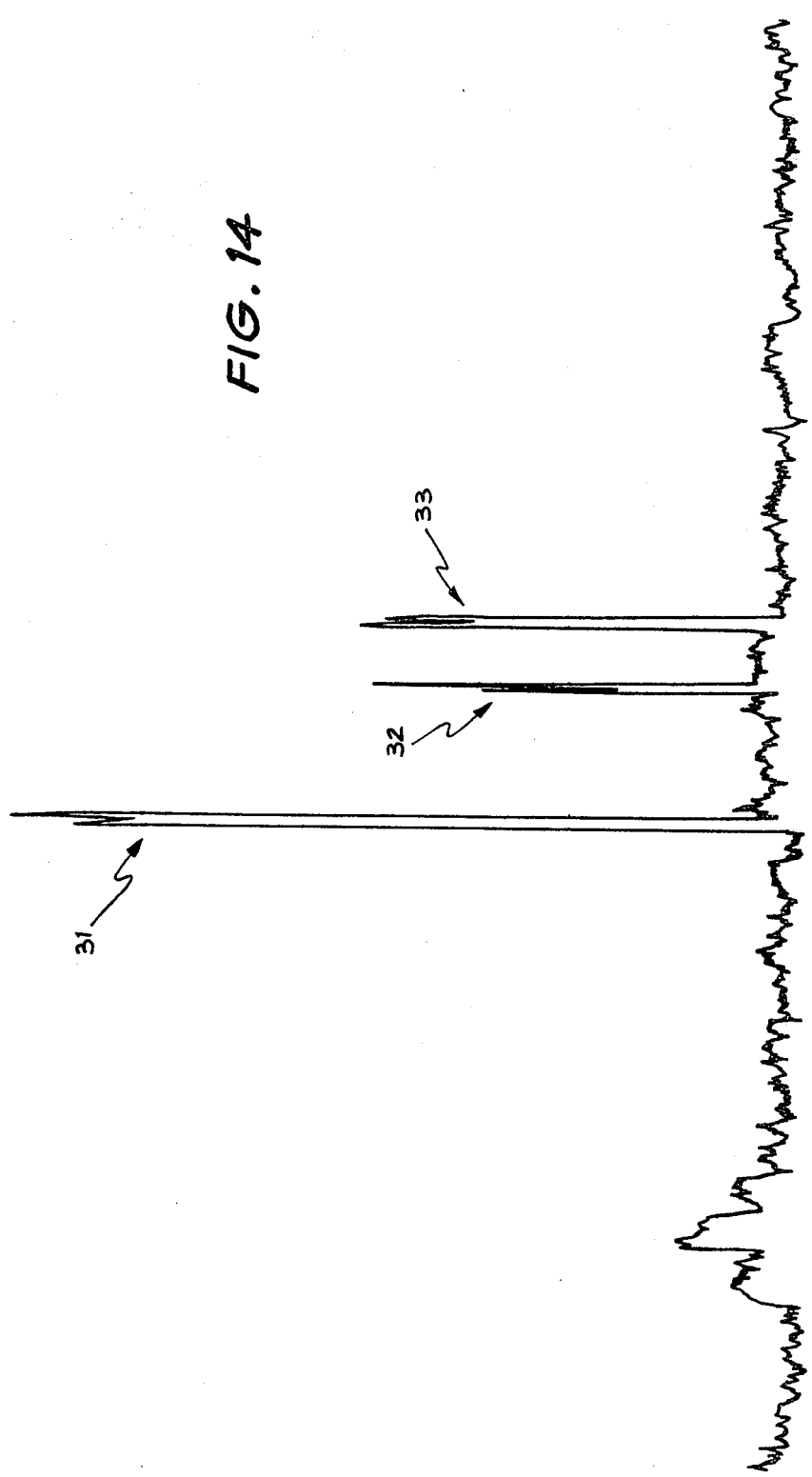
Figure 15:
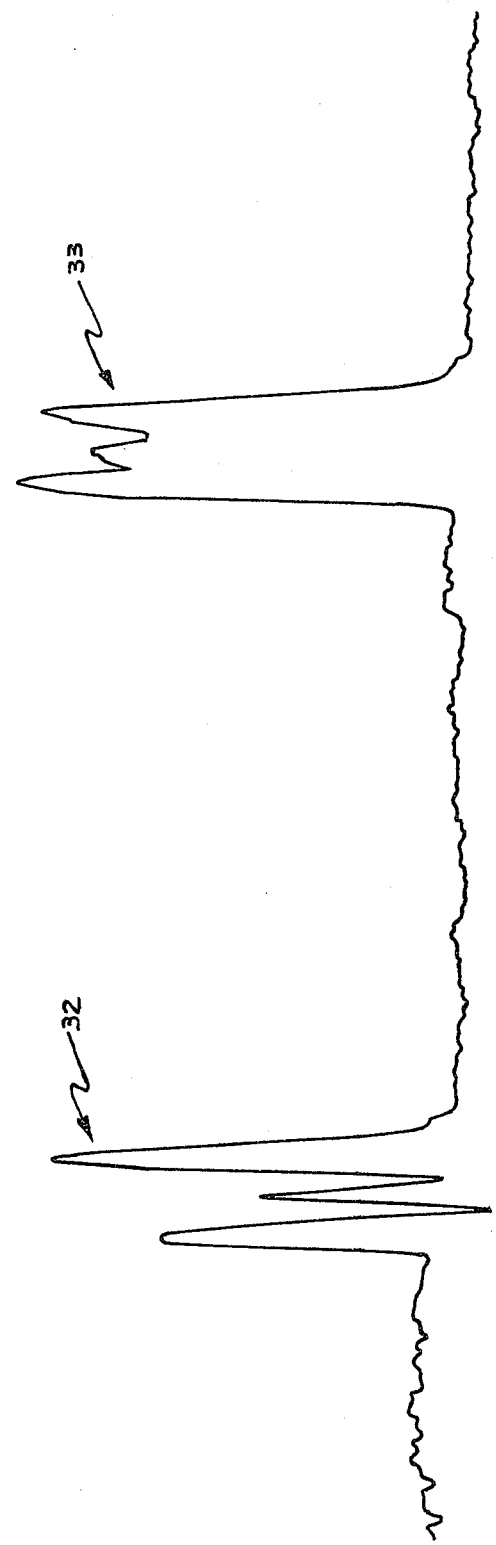
Figure 16:
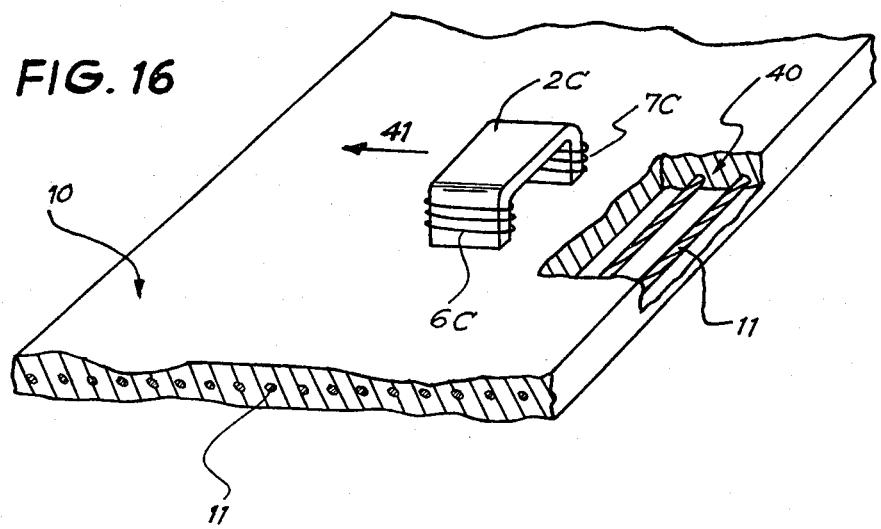
Figure 17:
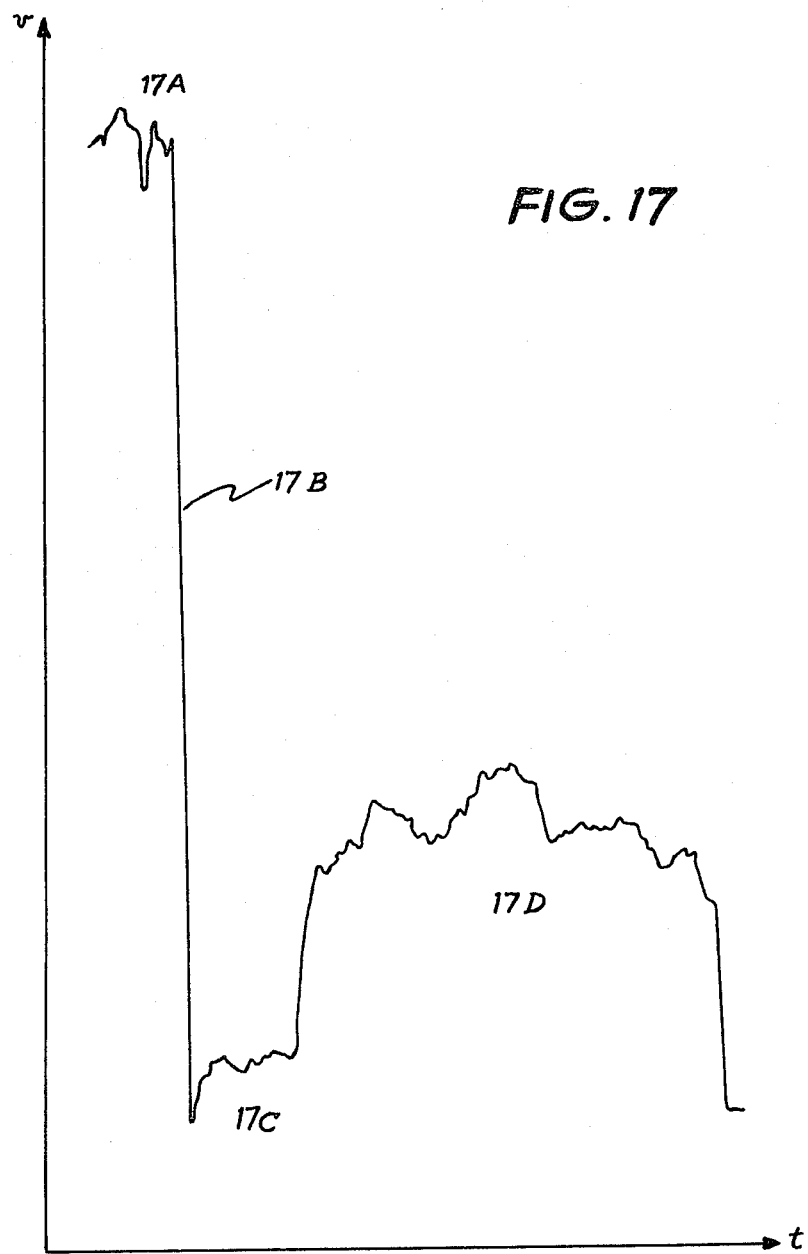

FIG. 7 is a circuit diagram of the differentiator block 19 and the latch block 20 of FIG. 4, FIG. 8 is a circuit diagram of the power supplies block 21 of FIG. 4, FIG. 9 is a graph of the output of the circuit of FIG. 6 as a function of time illustrating conveyor belt signature, FIG. 10 is a graph similar to FIG. 9 but with increased chart recorder speed, FIG. 11 is an X-ray result illustrating the splices indicated in FIG. 10, FIG. 12 is a graph of the actual cord number as revealed by the X-ray of FIG. 11, FIG. 13 is a graph of the output of the circuit of FIG. 6 illustrating by corrosion signature the condition of a small portion of a conveyor belt, FIG. 14 is a graph similar to FIG. 13 but illustrating by corrosion signature the same portion of the belt illustrated in FIG. 10, FIG. 15 is a graph similar to FIG. 14 but with increased chart recorder speed, FIG. 16 is a perspective view of a portion of a conveyor belt, FIG. 17 is a graph of the output of the circuit of FIG. 6 as a function of time when the transducer is moved transversely over the belt surface showing a covering wear signature of the wear of the rubber covering of the belt relative to the cord plane.

Figure 18:
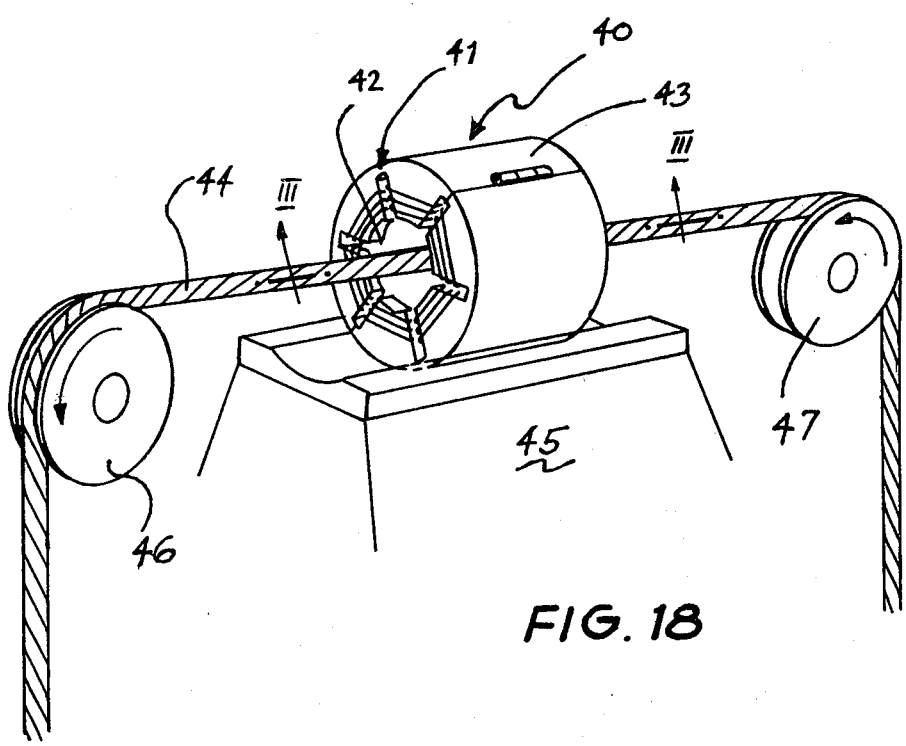
Figure 20:
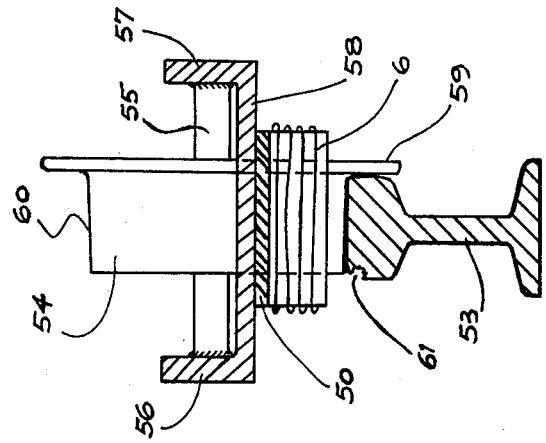
Figure 19:
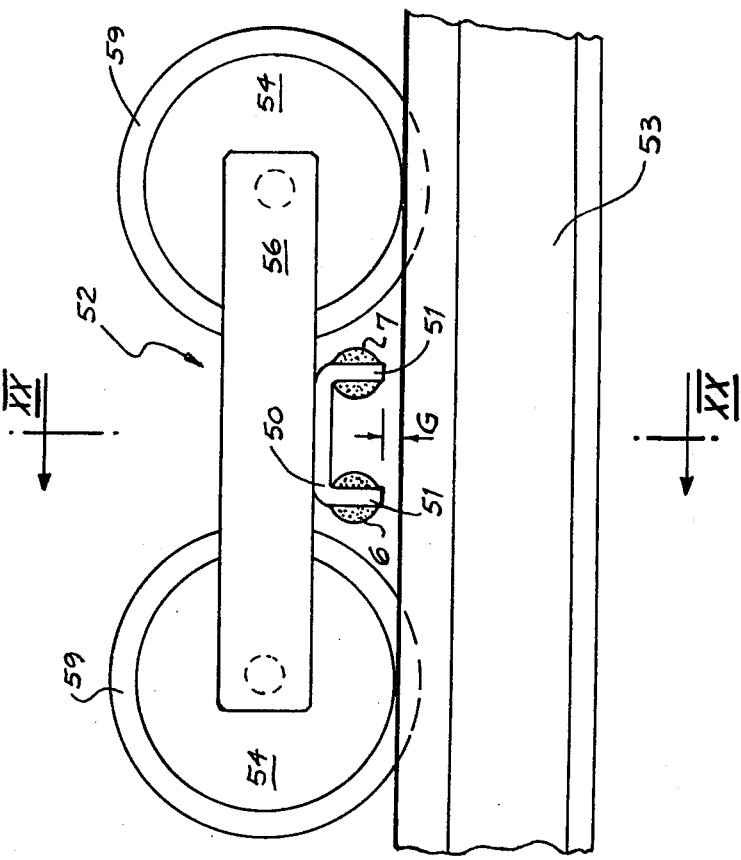

FIG. 18 is a schematic perspective view of apparatus of another embodiment used to measure wear of steel cables, FIG. 19 is a side elevation of apparatus of a still further embodiment used to measure wear in steel rails such as railway track, and FIG. 20 is a cross-sectional view taken along the line XX—XX of FIG. 19.

Referring now to FIGS. 1, 2, and 3, the apparatus of the preferred embodiment comprises a transducer assembly 1 formed from an upper magnetic yoke 2 of soft iron which is suspended below a wheeled carriage 3. The yoke 2 is formed from an inverted U-shaped channel member which has a plurality of slots 4 located at regularly spaced intervals in each of its side walls thereby forming a plurality of pole pieces 5. Each pole piece 5 carries either a field winding 6 or a sensing winding 7.

The carriage 3 is formed from heavy materials such as brass and is supported by a plurality of wheels 8 so that the pole pieces 5 are spaced a predetermined distance, from the upper surface 9 of a conveyor belt 10 having a plurality of longitudinally extending steel reinforcing cords 11.

A lower yoke 12 substantially identical with the upper yoke 2, is suspended from the carriage 3 by supports 13 (FIG. 2) located at each end of the transducer assembly 1. Like parts of the two yokes 2 and 12 are designated A and B respectively throughout the specification and drawings. As will become apparent from the description hereafter relating to conveyor belt signature analysis, both yokes are not essential to the present invention, since only one yoke is required for conveyor belt signature analysis.

The transducer assembly 1 is preferably located on the return run of the conveyor so that the upper yoke 2 is therefore located above the upper (clean) surface of the return run of the conveyor and between the forward and return runs of the conveyor. The lower yoke 2 is thus located below the return run of the conveyor.

The conveyor belt 10 is normally fabricated from non-magnetic material such as rubber or an elastomeric polyurethane. Preferably the dimension of the pole pieces 5A and 5B are such that approximately 10 of the cords 11 pass under each pole piece 5. The slots 4 reduce lateral eddy currents in the yokes 2 and 12 thereby resulting in better uniformity of the magnetic field distribution between the pole pieces 5A and 5B.

As seen in FIG. 3 the dimensions of each yoke 2 and 12 are preferably inter-related so that the yokes can be scaled to any size. Thus, for a width W for the yokes 2 and 12, the thickness T of the high permeability material from which the yoke is made, the pole length L (FIG. 1) and the gap G between the pole piece and the magnetic material (not just the air gap) are inter-related.

As a rough "rule of thumb" H is approximately one half of W, T is approximately one tenth H, L is approximately one and three quarters W, and G is approximately one fifth W. Each winding 6,7 is wound for a maximum flux density in the yoke 2,12.

Not only can the yoke of the preferred embodiment be scaled to any size but the shape of the yoke can be altered so that, for example, FIG. 3 could represent a section through a curved or toroidal yoke used to test tubular rubber pipe or steel cable.

Turning now to FIG. 4, the field windings 6A and 6B are respectively connected together in series across an AC supply which preferably comprises a 5 kHz sine wave oscillator 14 having an output of approximately 1 Vpp per field winding 6. However, the oscillator frequency can vary between 50 Hz and 50 kHz to suit the particular magnetically permeable member. In addition, a d.c. bias can be supplied to the field windings 6, and 6A by any conventional means (not illustrated) so that undirectional current rather than alternating current flows in the field windings 6 and 6A. However a time varying magnetic field is still created thereby. Another sine wave oscillator 15 is able to be connected, via switch S4, in parallel with oscillator 14 to produce an amplitude modulated output as will be explained hereafter. Each of the sensing windings 7A and 7B are respectively connected together in series. One end of each series connection is grounded and the other ends respectively provide inputs A and B from the upper yoke 2 and the lower yoke 12 to an input interface block 16.

In the preferred embodiment, a single field winding 6C and a single sensing winding 7C are also provided to permit the continuity of a single cord or the rubber wear profile to be detected. The output of single sensing winding 7C provides input C for input interface block 16.

With switch S4 open, the outputs of the sensing windings 7A, 7B comprise an amplitude modulated sine wave, the amplitude of which depends on the reluctance of the magnetic path(s) existing at any given time between each pair of pole pieces 5A, or 5B. The sine waves for each yoke are added in phase and pass through the input interface block 16 to the amplitude demodulator and null balance block 17, the output of which comprises a DC signal. The magnitude of this DC signal is a direct indication of the reluctance between the pole pieces 5 as a function of time. The reference potential of the DC signal is set by the block 17.

The output of the amplitude demodulator and null balance block 16 is passed through a gain and offset block 17. The output D from the gain and offset block 17 is compatible with an analog chart recorder (not illustrated).

The output of the gain and offset block 18 is also passed via a differentiator block 19 to latch block 20, the output of which provides a digital output E comparable with the analog indication provided by the output D block 18.

A power supplies block 21 converts the AC mains supply into a plurality of DC supply voltages which are then used where necessary throughout the circuit.

FIG. 5 illustrates the circuit details of the input interface block 16. Three switches S1, S2 and S3 are provided to permit the selection of any one of four possible signals to the amplitude demodulator and null balance block 17. These four signals are the output A from the sensing windings 7A of the upper yoke 2, the output B from the sensing windings 7B of the lower yoke 12, the sum of outputs A and B, and the output C from the single sensing winding 7C. Three operational amplifiers are used to provide some gain as well as some degree of isolation.

The circuit details of the amplitude demodulator and null balance block 17 are illustrated in FIG. 6, the circuit of the preferred embodiment incorporating five operational amplifiers. The last of these operational amplifiers preferably has a capacitor 22 connected (as illustrated) across the inputs of the operational amplifier. The capacitor 22 is of great assistance in removing vibrational noise from the output D.

FIG. 7 illustrates the circuit details of the differentiator block 19 and latch block 20 which, in the preferred embodiment, together include three differential amplifiers and four NAND gates. Similarly, FIG. 8 illustrates the circuit details of the power supplies block 21 which incorporates a mains isolation transformer, two diode bridges, and three integrated circuits.

In operation, the belt 10 typically travels at a speed of approximately 3 M/sec. and therefore the time taken for a particular point on the belt 10 to pass between adjacent pole pieces 5A or 5B is of the order of 100 ms. As indicated in FIG. 2, the magnetic field B produced by the field windings 6A, 6B, 6C passes longitudinally through the cords 11 between the pole pieces 5A, 5B. Where the steel cord 11 is intact, that is, its continuity has not been destroyed by a mechanical break or chemical corrosion, the reluctance of the magnetic path comprising the steel cord 11 and yoke 2 is relatively low and therefore the output of the sensing windings 7A, 7B and 7C is high. However, should the steel cord 11 be broken or corroded, the reluctance of the magnetic path is greatly increased and therefore the output of the sensing windings is correspondingly decreased.

The changes in the magnitude of the output of the sensing windings are reflected in the amplitude of the sine wave applied to the amplitude demodulater and null balance block 17. These changes in amplitude modulation are reflected in a change of the level of the output of the amplitude demodulator and null balance block 17 which results in a corresponding change in the amplitude of the output D of the gain and offset block 18.

With switch S4 closed, the output of oscillator 15 is mixed with the output of oscillator 14 so as to produce a resultant amplitude modulated signal which is applied to the field windings 6A, 6B. Preferably the modulation is 800 Hz on 5 kHz with 20% peak-to-peak modulation giving a modulation index of 0.2. However, modulation of the carrier frequency with a frequency of the order of 20% of the carrier frequency is sufficient.

The effect of an amplitude modulated signal being applied to the field windings 6A, 6B is to greatly reduce the electrical noise produced in the sensing windings 7A, 7B because of the vibration of the belt 10 towards and away from the pole pieces 5A, 5B as the belt travels. This effect is brought about because the output of the sensing windings is respectively increased and decreased as the belt 10, and hence cords 11, approach and recede from the pole pieces 5. At the same time the magnetic field penetrates into the belt 10 by a degree which varies in accordance with the instantaneous modulation amplitude.

However, the output of the sensing winding 7 does not directly reflect the modulation frequency due to the dependence on the output of the amount of steel cord 11 in the path of any particular line of magnetic flux passing between the poles 5.

Thus where an appreciable length of cord 11 lies in the magnetic flux path, small movements of either the cord 11 or the flux in response to vibration or modulation respectively will only have a negligible effect on the output of sensing winding 7.

However, where the flux nearly, or only just, links a cord 11 then small movements of the cord 11 or small changes in the flux penetration will significantly alter the reluctance of the magnetic path. The net result of this action is to smooth the output of the sensing winding 7 by damping relatively high frequency changes caused by vibration of the belt 10. Reductions in vibrationally caused noise of the order of 50% have been achieved.

The output D for signal A recorded at a relatively slow speed is illustrated in FIG. 9. Adjacent sections of the belt are indicated by adjacent peaks 31 in FIG. 9. The peaks 31 are caused by the additional steel present at the splice which joins each pair of adjacent belt sections.

It will be appreciated by those skilled in the art, that since the belt 10 is moving relative to the transducer assembly 1, the graph illustrated in FIG. 9 in fact represents a "map" of the belt 10 which is termed a "conveyor belt signature". The analog signal of output D indicated in FIG. 9 is also passed through the differentiator block 19 and thence through latch block 20 in order to provide a pulse at each time that the amplitude of the analog signal changes in a step-wise fashion. The pulses are then used to trigger a set-reset flip flop in order to provide a digital output E which is substantially comparable with the analog output illustrated in FIG. 9.

The graph illustrated in FIG. 9 is the result of operating the chart recorder at a low speed so that a relatively large portion or length of the conveyor belt is illustrated in the graph. If the chart recorder is operated at a faster speed, a much shorter length of the conveyor belt corresponds to an equivalent length of graph. This is the situation illustrated by the graph of FIG. 10 in which the output A of only sensing windings 7A is selected by means of switches S2 and S3 of FIG. 5 so as to produce a corresponding output D which is then graphed.

Commercially available conveyor belts are made up from a number of sections typically of the order of 300 m in length which are spliced together to form a continuous belt. In addition, the sections are often repaired by cutting out a portion and splicing in a new portion. As seen in FIG. 10, each of these splices in the belt results in a peak. Thus the "conveyor belt signature" graph of FIG. 10 includes three peaks 31, 32 and 33 which indicate three adjacent splices in the belt. FIG. 10 also indicates the condition of the reinforcing cords within the belt. The graph of FIG. 10 provides an excellent visual record of the nature of the splices in the belt. Thus because the peaks 31 and 33 of FIG. 10 have a substantially uniform amplitude, this is indicative of a uniform overlap of the steel cords within the splice so that the reluctance of the conveyor belt is substantially constant for the length of the splice. However, this is not the case for the splice corresponding to peak 32 and since the amplitude of the peak 32 is greatly reduced at two positions within the peak 32, it is clear that at the corresponding two locations within the conveyor belt there is not an acceptable degree of overlap of the steel cord within the splice. Thus the strength of the splice is substantially reduced and FIG. 10 can be regarded as illustrating three splice signatures in the form of the three peaks.

The results of X-ray analysis of the conveyor belt splice which corresponds to peak 32 of FIG. 10 are illustrated in FIG. 11. To the left and right of FIG. 11 can be seen the spaced steel cords within the unspliced portions of the conveyor belt which are illustrated immediately to the left and right respectively of the peak 32 of FIG. 10. The three regions of high amplitude of peak 32 correspond to the three regions of over-lapping cords illustrated in FIG. 11 and these three regions are separated by means of two other regions of very substantially reduced numbers of reinforcing cords. The type of splice corresponding to peak 32 is termed a 3-stage splice. These two regions correspond to the two regions of low amplitude contained within the peak 32. The two weakened regions within the splice have substantially reduced the strength of the conveyor belt and the belt, being under tension, has begun to neck, or reduce in width, at the location of the defective splice corresponding to peak 32. This can be seen from a consideration of FIG. 11 where the width of the conveyor belt is reduced in the centre of that portion of the conveyor belt which is X-rayed.

FIG. 12 shows a graph of the cord density of the peak 32 of FIG. 10 as determined by actually counting the cords revealed by the X-ray of FIG. 11. The solid line in FIG. 12 shows the actual counted numbers of cords whilst the broken line indicates the expected graph produced by a chart recorder which, of necessity, must possess some inertia. Bearing in mind the differences in scale between FIGS. 10 and 12, it is clear that there is excellent correlation between the broken line of FIG. 12 and the graph of FIG. 10.

The distance between adjacent peaks 32 and 33 of FIG. 10 corresponds to approximately 20 m which length was inserted into the conveyor belt in order to repair same. However, subsequent analysis of the repair in accordance with the foregoing has indicated that one of the splices of the repair was faulty. Thus, such faulty splice work is able to be determined at the time of making the repair and therefore a defective repair can be corrected on the one occassion at which the belt is stopped. This is far better than stopping the belt for a repair and then a short time later incurring the economic cost of a further stoppage to correct a further fault in the conveyor belt brought about by failure of one of the splices in the repair.

Since the conveyor belt must be stopped in order to X-ray the belt, and this procedure is slow, cumbersome and expensive, the graph of FIG. 10 provides a particularly valuable tool for the analysis of splices in conveyor belts. In particular, for each peak, the area under the curve of the peak is approximately proportional to the strength of the splice and hence is proportional to the safety margin of the splice. Therefore a simple graphical analysis, rather than a cumbersome and expensive X-ray, can be used to determine whether or not a particular splice should be accepted or replaced.

The conveyor belt signature of a conveyor belt is unique and will be reproduced each time the conveyor belt passes under the upper yoke 2, after each complete revolution of the belt. Thus a signature in the form of graph 10 may be taken at different times for the same belt and the various signatures compared. If there has been no corrosion in the belt and also no substantial wear of the rubber covering of the belt, then the signatures taken at different times will be substantially identical. Thus any marked change in the amplitude of the conveyor belt signature can be used as an early warning that the condition of the belt has deteriorated and therefore failure is likely unless steps are taken to repair that location of the belt.

Since the graphs of FIGS. 9 and 10 are directly proportional to the reluctance between the pole pieces 5A, it will be apparent to those skilled in the art that as the rubber covering of the belt wears, so the steel reinforcing cords within the belt will be spaced more closely to the pole pieces 5A thereby decreasing the reluctance of the magnetic path between the pole pieces 5A. Thus conveyor belt signatures taken at different times provide a measure as to the degree of wear of the rubber covering of the belt since the change in reluctance of the belt brought about by wear of its rubber covering will be very much less than the change in reluctance of the belt brought about by corrosion or breakage of the reinforcing cords.

A problem arises, however, in relation to conveyor belts for which there is no previous conveyor belt signature with which the graphs of FIGS. 9 and 10 can be compared. In the absence of such a comparision one cannot be certain that a change in the amplitude of the graph (and hence belt reluctance) has been caused by a change in the condition of the reinforcing cords or caused by, for example, a patch of abnormally high rubber wear.

In order to overcome this problem, the lower yoke 12 is provided and the two signals A and B are added together in anti-phase. It would be apparent to those skilled in the art that if the upper surface of the conveyor belt is worn, then the steel reinforcing cords will be closer to pole pieces 5A but further away from pole pieces 5B. Thus the reluctance between pole pieces 5A will be decreased whereas the reluctance between pole pieces 5B will be increased by a corresponding amount.

Thus, adding the signals A and B in anti-phase automatically compensates for changes in the thickness of the rubber covering caused by wear. In addition, this procedure also overcomes changes in reluctance caused by the fact that the steel cords may not at all times be centrally located within the belt at the time of its manufacture. This manufacturing defect can produce changes in the graphs 9 and 10 of the conveyor belt signature which are capable of being misinterpreted as due to corrosion in the steel cords.

FIGS. 13 and 14 are graphs illustrating the output D of FIG. 6 in the situation where switches S1 to S3 of FIG. 5 are connected so as to provide the summed output of A and B.

The output D for signal A+B (with signal A and signal B both being identically calibrated by use of potentiometer R5 of FIG. 5) recorded at relatively high speed on a chart recorder as a function of time is illustrated in FIG. 13. The first portion 9A of the trace indicates that none of the cords have been corroded, the second portion 9B indicates that 6 cords of the total of approximately 60 or 70 cords in the belt are corroded. The next portion 9C indicates that 11 cords of the belt are corroded and therefore this portion of the belt should be replaced since it is likely that this portion of the belt will fail in the near future. The next portion 9D indicates that none of the cords are corroded whilst the next portion 9E indicates that there is a relatively short break in many of the cords, and so on. A splice 31 joining adjacent portions of the belt is also shown. The duration of portion 9C corresponds exactly to a length in the belt 10 which should be replaced. In order to determine the precise location of the length to be replaced it is necessary to correlate the start of the chart recording with the initial portion of the belt 10 to pass under the transducer assembly 1, usually a splice is marked as a reference.

In FIG. 14 the chart recorder is operated at a slower speed than in FIG. 13 and also in respect of the same piece of belt as is the subject of FIG. 10. The graphs of FIGS. 13 and 14 are termed corrosion signatures since although peaks 31, 32 and 33 of FIG. 10 are clearly shown in FIG. 14, the variation in the output brought about by rubber wear in FIG. 10 has been eliminated in FIG. 14.

FIG. 15 is a graph similar to FIG. 14 save that the chart recorder is operated at a higher speed. Again the same portion of conveyor belt is used so that peaks 32 and 33 are again produced. The relatively flat portions of the graph of FIG. 15 between the peaks 32 and 33 indicate that none of the cords in the belt are corroded and that the only defect in the belt is the faulty splice corresponding to peak 32.

Turning now to FIGS. 16 and 17, the need sometimes arises to determine the transverse profile of the rubber on a belt. This comes about because conveyor belts are typically supported by three rollers, a central horizontal roller and an inclined roller positioned at each end of the central roller so as to form a generally U-shaped trough to which the loaded conveyor belt conforms. This arrangement gives rise to increased wear of the rubber on the conveyor belt which, after a period of time, results in a characteristic W-shape for the conveyor belt when viewed in transverse cross section.

The profile of the belt can be determined by use of the single transducer 6C, 7C of FIG. 4 which is schematically illustrated as yoke 2C in FIG. 16. Also schematically illustrated in FIG. 16 is a length of conveyor belt 10 having steel reinforcing cords 11. At 40, a region of the rubber covering of the belt is cut away in order to expose the cords 11 and the yoke 2C is moved from side to side across the conveyor belt in a transverse direction, that is normal to the longitudinal axis of the belt, in the direction of arrow 41.

The output of the sensing winding 7C as a function of time during the above described motion is graphed in FIG. 17 and termed a covering wear signature since it indicates the wear of the rubber covering of the conveyor belt. The very high output 17A caused initially is brought about by the yoke 2C being substantially in contact with some of the cords 11 thereby producing a magnetic path for the yoke 2C of very low reluctance.

An abrupt step 17B is caused by the lifting of the yoke 2C onto the upper surface of the rubber of the conveyor belt 10 which results in output 17C. As the yoke 2C is moved across the load carrying centre portion of the belt 10, the output 17D is produced showing the substantially W-shaped worn region at the centre of the belt.

Clearly, the arrangement of FIG. 16 permits the wear of the rubber covering of the belt to be ascertained in the transverse direction whilst the apparatus of FIG. 1 permits the wear to be ascertained in the longitudinal direction of the belt. This is of assistance in the design and study of supporting roller arrangements for conveyor belts.

Turning now to FIG. 18, an annular embodiment of the present invention useful for testing cylindrical bodies such as steel cables, coated steel cables, rubber tubes with steel reinforcing cables, and even concrete beams and columns with steel reinforcing rods.

In the embodiment illustrated in FIG. 18 an annular yoke 40 is formed by bending a piece of U-shaped iron channel to form an annulus. A plurality of radial slots 41 are cut in the yoke 40 to form pole pieces 42 which carry field and sensing windings 6,7 as before. The yoke 40 is preferably formed from two semi-circular pieces connected together by a hinge 43. Thus a view taken along the line III—III of FIG. 18 will resemble FIG. 3.

The hinge 43 permits the yoke 40 to be opened and placed over a steel cable 44 so that the cable 44 is substantially co-axial with the yoke 40, which is supported by any convenient structure 45. The cable 44 can be either bare or covered by means of a coating of plastics, rubber, tar or the like. Such cables find wide application in cranes, winches and other such apparatus. Since these cables carry a heavy load during operation, it is very desirable to known if any of the steel strands (not illustrated) from which the cable 44 is formed, are broken, or worn, or abraded or plastically deformed thereby indicating probable imminent cable failure.

In order to permit relative movement between the yoke 40 and cable 44, it is desirable to locate the yoke 40 between two pulleys 46 and 47 so that the cable 44 can pass over the pulleys 46, 47 whilst still remaining substantially co-axial with the yoke 40. In this way substantially all of the cable 44 can be passed through the yoke 40.

During this operation, the reluctance path of the yoke which includes a sound cable will be substantially constant and therefore the output of the sensing windings will also be substantially constant. However, where one or more strands of the cable are broken or worn, then the cable reluctance is changed resulting in a changed sensing winding output. Furthermore, wear of bare cables with time so that the overall diameter of the cable is decreased can also be detected due to increased reluctance of the cable produced by its reduced cross-sectional area.

FIGS. 19 and 20 illustrate apparatus of another embodiment which is useful in the testing of steel railway lines for wear and structural defects. The apparatus takes the form of a yoke 40 having only two pole pieces 51 which carry field and sensing windings 6 and 7 respectively.

The pole pieces 51 are supported by a carriage assembly 52 so that a substantially constant air gap G is maintained between the downwardly directed faces of the pole pieces 51 and the upper surface of a steel rail 53 which typically forms part of a railway track or permanent way.

The carriage assembly 52 includes two jockey wheels 54 which each rotate about a corresponding axle 55 carried by two transoms 56 and 57. A cross bar 58 extends between the transoms 56 and 57 and supports the yoke 50. The jockey wheels 54 have an internal annular flange 59 and a cylindrical surface 60 which bears on the upper surface of the rail 53.

The carriage assembly 52 depends in any conventional fashion from a bogey (not illustrated) so that the jockey wheels 54 always bear against the rail 53. This can be achieved by downwardly resiliently biasing the carriage assembly 52 against the bogey.

As the carriage assembly 52 moves along the rail 53, the field winding 6 induces a time varying magnetic field in the rail 53 which, in turn, induces a voltage in the sensing winding 7 which is dependent upon the reluctance of the rail 53. Thus not only can notches 61 and similar defects in the rail 53 be detected but wear of the rail 53 can also be detected. In both instances a change in the amount of magnetic material (steel) present in the rail 53 is brought about and this change results in a change in reluctance detectable by the sensing winding 7.

The foregoing describes only some embodiments of the present invention and modifications, obvious to those skilled in the art, may be made thereto without departing from the scope of the present invention. For example, the integrity and depth of steel reinforcing rods embedded in concrete columns and beams can be determined by passing the carriage 3 containing only the upper yoke 2 over the surface of the concrete column or beam and obtaining an output as described above. Such an output will be indicative of the condition of the steel reinforcing within the concrete member and hence indicative of the strength of the member. Similarly, a toroidal yoke as illustrated in FIG. 18 can be used to test the integrity and continuity of steel reinforcement within cylindrical or tubular non-magnetic bodies such as cylindrical columns of reinforced concrete or rubber tubing reinforced with steel cords.

What is claimed is:

1. Apparatus for monitoring the integrity of an elongate magnetically permeable member having a longitudinal axis, said apparatus comprising a magnetically permeable yoke disposed in a plane substantially transverse to the longitudinal axis of said magnetically permeable member, said yoke having a substantially U-shaped transverse cross-section and a plurality of pairs of pole pieces formed by slots in said yoke, the poles of each pair of pole pieces lying in a direction substantially parallel to the longitudinal axis of said permeable member, one pole piece of each pair of said pole pieces carrying a field winding and the other pole piece of each said pair of pole pieces carrying a corresponding sensing winding; spacing means to maintain a substantially predetermined spacing between said elongate member and said pole pieces and to permit movement of said yoke relative to longitudinal axis of said member; current generating means connected to said field windings to induce a time varying magnetic field passing through said elongate member between each said pair of pole pieces; and sensing means connected to said sensing windings to sense the voltage induced therein by said magnetic field.

2. Apparatus for monitoring the integrity of an elongate magnetically permeable member having a longitudinal axis and being of a structure which does not generate substantially effective eddy currents when subjected to a time varying magnetic field, said apparatus comprising a magnetically permeable yoke disposed in a plane substantially tranverse to the longitudinal axis of said magnetically permeable member, said yoke having a substantially U-shaped traverse cross-section and a plurality of pairs of the pieces formed by slots in said yoke, the poles of each pair of pole pieces lying in a direction substantially parallel to the longitudinal axis of said permeable member, one pole piece of each pair of said pole pieces carrying a field winding and the other pole piece of each said pair of pole pieces carrying a corresponding sensing winding; spacing means to maintain a substantially predetermined spacing between said elongate member and said pole pieces and to permit movement of said yoke relative to the longitudinal axis of said member; current generating means connected to said field windings to induce a time varying magnetic field passing through said elongate member between each said pair of pole pieces thereby to generate a substantially eddy current free magnetic field; and sensing means connected to said sensing windings to sense the voltage induced therein by said mangetic field, said sensing means being responsive to the eddy current free magnetic induction.

3. Apparatus as claimed in either claim 1 or 2 wherein said yoke is annular, said slots are substantially radial and said pole pieces define an interior substantially co-axial cylindrical cavity of internal diameter sufficient to receive said elongate magnetic member.

4. Apparatus as claimed in claim 3 wherein said yoke is formed from least two sections movable with respect to one another so that said yoke can be opened and closed to place said yoke around said elongate magnetic member.

5. Apparatus as claimed in either claim 1 or 2 wherein said yoke comprises a substantially straight U-shaped channel with said slots being cut in the sides thereof to form said pairs of pole pieces.

6. Apparatus as claimed in claim 5 wherein said field windings are connected together in series across said current generating means and said sensing windings are connected together in series across said sensing means.

7. Apparatus as claimed in claim 5, wherein said elongate permeable member comprises a conveyor belt having elongate permeable reinforcing members and said spacing means comprises a wheeled carriage which carries said yoke and is positioned on one surface of said conveyor belt and supported thereby with said yoke extending tranversely across said belt.

8. Apparatus as claimed in claim 7, wherein said carriage includes a further, substantially identical yoke, said yoke and said further yoke being substantially parallel with said further yoke being located adjacent to the other surface of said belt.

9. Apparatus as claimed in claim 8, wherein said sensing means adds the output of all said sensing windings together with the output of the sensing windings of said further yoke being added in anti-phase.

10. Apparatus as claimed in either claim 1 or 2, wherein said current generating means comprises an oscillator having a frequency of from 50 Hz to 50 kHz.

11. Apparatus as claimed in claim 10, wherein the output of said oscillator is amplitude modulated with a frequency approximately 20 percent of the frequency of said oscillator.

12. Apparatus as claimed in claim 10, wherein said sensing means is tuned to the frequency of said oscillator and comprises an amplitude detector.

13. Apparatus as claimed in claim 12, wherein said sensing includes a logic circuit having differentiator means connected to said amplitude detector and latching bistable circuit means connected to said differentiator means, said latching bistable means having a digital output dependent upon the reluctance of said magnetically permeable member.

14. Apparatus as claimed in claim 5, wherein each said pair of pole pieces comprises a generally rectangular portion of said yoke, and has a substantially constant thickness, wherein the length of each said pole piece is approximately half the distance between said pole pieces, the thickness of said portion is approximately one tenth said pole piece length, the width of each said pole piece is approximately one and three quarters times said distance between said pole pieces and said predetermined spacing between said pole pieces and said elongate member is approximately one fifth of said distance between said pole pieces.

15. Apparatus as claimed in claim 1, wherein said elongate magnetically permeable member is covered with non-magnetic material.

16. Apparatus as claimed in claim 10, wherein said sensing means comprises an a.c. detector circuit connected to the sensing windings for detecting the fall of the induced voltage below a predetermined level for a predetermined time.

17. Apparatus as claimed in claim 16, wherein said a.c. detector circuit comprises an integrator circuit for integrating said induced voltage over an extended period of time to establish a reference signal level, a comparator circuit for comparing said reference level with the substantially instantaneous induced voltage, and output means for signifying when said substantially instantaneous induced voltage falls below the reference level by a predetermined degree.

18. A method of monitoring the integrity of a conveyor belt having a longitudinal axis and a plurality of elongate magnetically permeable reinforcing cords covered with non-magnetic material, said method comprising the steps of locating a magnetically permeable yoke adjacent one surface of said conveyor belt and disposed in a plane substantially transverse to said longitudinal axis, said yoke having a substantially U-shaped transverse cross-section and a plurality of pairs of pole pieces formed by slots in said yoke, the poles of each pair of pole pieces lying in a direction parallel to the longitudinal axis of said permeable member, one pole piece of each of said pair of pole pieces carrying a field winding and the other pole piece of each said pair of pole pieces carrying a corresponding sensing winding; causing a relative movement between said conveyor belt and said yoke while maintaining a substantially constant spacing between said yoke and said conveyor belt; supplying a time varying electric current to each of said field windings to induce a time varying magnetic field between the pole pieces of each pair of pole pieces, said magnetic field passing through said cords; and sensing changes in the voltage induced in each of said sensing windings caused by changes in the reluctance path containing said yoke and said cords.

19. The method as claimed in claim 18, wherein the voltages induced in all said sensing windings are added together in phase.

20. The method as claimed in claim 18 wherein a further yoke is located adjacent the other surface of said conveyor belt, said yoke and said further yoke being substantially identical; said time varying electric current is supplied to each of the field windings of said further yoke to induce a further time varying magnetic field between the pole pieces of each pair of pole pieces of said further yoke, said further magnetic field passing through said cords; and sensing changes in the voltages induced in each of the sensing windings of said further yoke caused by changes in the reluctance path containing said further yoke and said cords.

21. The method as claimed in claim 20, wherein the voltages induced in all said sensing windings are added together with the voltages induced in the sensing windings of said yoke being added in phase and the voltages induced in the sensing windings of said further yoke being added in anti-phase.

22. The method as claimed in claim 20, wherein said yoke and said further yoke are carried by a wheeled carriage supported on an upper surface of said conveyor belt.

23. The method as claimed in claim 18, wherein said time varying electric current has a frequency in the range of from 50 Hz to 50 kHz.

24. The method as claimed in claim 23, wherein said time varying electric current is amplitude modulated with a frequency approximately 20 percent of the frequency of said time varying electric current.

25. A method as claimed in any one of claims 18 to 24 wherein the yoke is located transversely across substantially the entire conveyor belt.

* * * * *